United States Patent [19]

Crawford et al.

[11] Patent Number: 4,672,061

[45] Date of Patent: Jun. 9, 1987

[54] ANTIINFLAMMATORY COMPOSITIONS AND METHODS

[75] Inventors: Thomas C. Crawford; Stanley L. Keely, both of Ledyard; David L. Larson, East Lyme; Joseph G. Lombardino, Niantic; James J. Maciejko, Mystic, all of Conn.

[73] Assignee: Pfizer Inc., New York, N.Y.

[21] Appl. No.: 821,183

[22] Filed: Jan. 21, 1986

Related U.S. Application Data

[60] Division of Ser. No. 695,590, Jan. 28, 1985, Pat. No. 4,579,846, which is a continuation-in-part of Ser. No. 659,602, Oct. 11, 1984, abandoned.

[51] Int. Cl.$^4$ ............................................. A61U 31/54
[52] U.S. Cl. .................................................... 514/222
[58] Field of Search ......................................... 514/222

[56] References Cited

U.S. PATENT DOCUMENTS

| | | | |
|---|---|---|---|
| 4,132,788 | 1/1979 | Wong | 424/274 |
| 4,207,340 | 6/1980 | Gardocki | 424/317 |
| 4,233,313 | 11/1980 | Gardocki | 424/274 |
| 4,233,314 | 11/1980 | Gardocki | 424/317 |
| 4,233,315 | 11/1980 | Gardocki | 424/317 |
| 4,233,316 | 11/1980 | Gardocki | 424/317 |
| 4,233,317 | 11/1980 | Gardocki | 424/317 |
| 4,234,601 | 11/1980 | Gardocki | 424/319 |
| 4,242,353 | 12/1980 | Gardocki | 424/274 |

FOREIGN PATENT DOCUMENTS 109281  5/1984  European Pat. Off. .

OTHER PUBLICATIONS

Seegers et al., J. Pharm. Pharmacol. 30, 84 (1978).
Seegers et al., J. Pharm. Pharmacol. 31, 840 (1979).
Seegers et al., Adv. Prost. Thromb. Res. 8, 1547 (1980).
Konturek et al., Gut 23, 536 (1982).
Stern et al., Gastroenterology 86, 728 (1984).
van Kolfschoten et al., Agents and Actions 12, 247 (1982).
Van Kolfschoten et al., Tox. Appl. Pharm. 69, 37 (1983).
Fielding et al., Eur. Surg. Res. 9, 252 (1977).
Kasuya et al., Japan J. Pharmacol. 29, 670 (1979).
McGreevy et al., Surg. Forum 28, 357 (1977).
Rudd et al., Curr. Med. Res. Opin. 6, (suppl. 9), 37 (1980).
Hoff et al., Scand. J. Gastroent. 16, 1041 (1981).
Leitold et al., Advances in Experimental Ulcer, Umehara and Ito, editors, ICEU, Tokyo, 1982, pp. 27-36.
Leitold et al., Arch. Pharmacol. 316 (suppl.), R50 (1981).
Leitold et al. Arzneim, Forsch/Drug Res. 34, 468 (1984).

Primary Examiner—Stanley J. Friedman
Attorney, Agent, or Firm—Charles J. Knuth; Albert E. Frost; Robert K. Blackwood

[57] ABSTRACT

An improved antiinflammatory composition and method of treating inflammation which employs a combination of antiinflammatory piroxicam, or a pharmaceutically acceptable salt thereof, with analgesis acetaminophen, antidepressant doxepin, bronchodilator pirbuterol, minor tranquilizer diazepam, or antihypertensive trimazosin.

6 Claims, No Drawings

ANTIINFLAMMATORY COMPOSITIONS AND METHODS

CROSS REFERENCE TO RELATED APPLICATION

This application is a division of copending application Ser. No. 695,590, filed Jan. 28, 1985, now U.S. Pat. No. 4,579,846, which is a continuation-in-part of application Ser. No. 659,602, filed Oct. 11, 1984 now abandoned.

BACKGROUND OF THE INVENTION

The present invention is concerned with an improved antiinflammatory composition and method of treating inflammation which employs antiinflammatory piroxicam, or a pharmaceutically acceptable salt thereof (particularly the ethanolamine salt) in combination with analgesic acetaminophen, antidepressant doxepin, bronchodilator pirbuterol, minor tranquilizer diazepam, or antihypertensive trimazosin or a related compound. The generic names used here and elsewhere herein are from the USAN and the USP Dictionary of Drug Names, 1961-1981, Griffiths et al., ed., U.S. Pharmacopeial Convention Inc., Rockville, Md., 1984, have subsequently been assigned and published as official USAN names, and/or appear in The Merck Index 10th Edition.

Gastrointestinal irritation, including ulcers, is a side effect commonly associated, to one degree or another, with antiinflammatory agents. In many cases, individuals requiring such antiinflammatory treatment are precluded from enjoying the benefits thereof because of their susceptibility to such side effects. The present combination of piroxicam with one or another of the medicinal agents defined above permits desirable antiinflammatory therapy while preventing or ameliorating said gastrointestinal irritation or ulcers.

Acetaminophen has. been previously reported to reduce the ulcerogenicity of aspirin [Sugers et al., J. Pharm. Pharmacol. 30, 84 (1978); ibid. 31, 840 (1979); and Adv. Prost. Thromb. Res. 8, 1547 (1980)], or of acidifed aspirin [Konturek et al., Gut 23, 536 (1982)]. However, indomethacin reversed the protective effect of acetaminophen when given with acidified aspirin (loc. cit.). In later studies, it was reported that acetaminophen reduced the ulcerogenicity of indomethacin and aspirin, but not of phenylbutazone or glafenine, and of ibuprofen only at the highest dose (800 mg/kg) of the latter compound [van Kolfschoten et al., Agents Actions 12, 247 (1982); Toxicology Applied Pharm. 69, 37 (1983)]. Acetaminophen in combination with ketoprofen and other particular antiinflammatory agents has been reported to provide an analgesic effect which is greater than a simple additive effect (U.S. Pat. Nos. 4,233,313 to 4,233,317; 4,234,601; 4,207,340; and 4,242,353). While we are aware of no literature reports concerning the combination of acetaminophen with piroxicam or any other oxicam for any purpose, we have been advised that a piroxicamacetaminophen combination has been recently marketed in Argentina.

Bronchodilators salbutamol (albuterol), phenylephrine and isoproterenol, but not propranolol, have been reported to inhibit formation of indomethacin-induced ulcers in animals [Fielding et al., Eur. Surg. Res. 9, 252 (1977); Kasuya et al., Japan J. Pharmacol. 29, 670 (1979)]. In another study, administration of isoproterenol to a chambered section of a dog's fundus reduced or prevented aspirin-induced tissue damage [McGreevy et al., Surg. Forum 28, 357 (1977)]. There are no known prior reports concerning the effect of bronchodilator pirbuterol on antiinflammatory agents.

Antidepressant doxepin has also been reported to have gastric antisecretory activity and to be as effective as cimetidine in the treatment of duodenal ulcers in humans [Hoff et al., Curr. Med. Res. Opin. vol. 6, supplement 9, page 36 (1980); Scand. J. Gastroent. 16, 1041 (1981)]. It has also been reported that doxepin shows antiulcer and antisecretory activity in rats and dogs; and that it significantly reduced the ulcerogenic potential of indomethacin, diclofenac and aspirin in water-immersion restraint-stressed rats [Leitold et al. Arch. Pharmacol. 316 (supplement), R50, abstract 199 (1981); Leitold et al., Advances in Experimental Ulcer, Umehara and Ito, editors, ICEU, Tokyo pp. 27–36 (1982); Arzneim-Forsch/Drug Res. 34, 468 (1984)].

Major tranquilizer and antipsychotic chlorpromazine has been reported to reduce indomethacin-induced gastric ulcers in rats [Kasuya et al. loc. cit. (1979)]. However, there are no known prior reports concerning the use of an antihypertensive agent such as trimazosin or a minor tranquilizer such as diazepam in reducing gastric side-effects induced by nonsteroidal antiinflammatory agents.

Phospholipids have also been reported to reduce gastrointestinal distress (damage to the mucous membrane, gastric ulcer formation) when combined with nonsteroidal antiinflammatory agents, particularly phenylacetic or phenylpropionic acid derivatives such as ibuprofen, naproxen, diclofenac and fluribprofen [Ghyczy et al., U.S. Pat. No. 4,369,182 (1983)], as have antiulcer pirenzepine [Leitold et al., Therapiewoche 27, pp. 1532–1548 (1977); German Patent Application No. 2,708,520] and histamine-$H_2$ antagonist (gastric acid antisecretory, antiulcer) compounds such as ranitidine, cimetidine and 1-methyl-5-[[3-[3-(1-piperidinylmethyl)-phenoxy]-propylamino]]-lH-1,2,4-triazole-3-methanol, which have been previously combined with indomethacin and other antiinflammatory agents for this purpose. See, for example, U.K. Patent Application Nos. 2,105,193 and 2,105,588; and Lovelace, U.S. Pat. No. 4,230,717.

Co-pending U.S. patent application Ser. No. 659,733 by Lombardino, filed concurrently with the grandparent of the instant application, describes improved antiinflammatory salts of piroxicam, including those with trimazosin, doxepin, N-demethyldoxepin, isoproterenol and pirbuterol.

SUMMARY OF THE INVENTION

The present invention concerns an improved antiinflammatory composition which comprises an antiinflammatory amount of piroxicam, or a pharmaceutically acceptable salt thereof (particularly the ethanolamine salt), in combination with a piroxicam-induced gastric irritation and ulcer inhibiting amount of a compound selected from the group consisting of acetaminophen, doxepin, pirbuterol, diazepam, fanetizole, trimazosin and related compounds, and the pharmaceutically-acceptable salts thereof.

The present invention is also concerned with an improved method for the treatment of inflammation in a mammal, including man, which comprises, in addition to treatment with an antiinflammatory amount of piroxicam, treatment with a gastric antiirritation and ulcer inhibiting amount of acetaminophen, doxepin, pirbuterol, diazepam, fanetizole, trimazosin, or a pharmaceutically-acceptable salt thereof.

DETAILED DESCRIPTION OF THE INVENTION

The antiinflammatory agent of the present invention, piroxicam, is known. For example, The Merck Index 10th Ed., 1983 contains a monograph concerning piroxicam (no. 7378), as does the Physicians' Desk Reference (PDR), 38th Ed., pp. 1556–1557 (1984). The preferred ethanolamine salt of piroxicam is specifically disclosed in U.S Pat. No. 4,434,164.

The compounds of the present invention which we have found to inhibit piroxicam-induced gastric irritation and ulcers are also known compounds. Acetaminophen is a proprietory analgesic (The Merck Index 10th Ed., monograph no. 39; see also the PDR, 38th Ed., p. 2096). Doxepin is an antidepressant, marketed in the form of its hydrochloride salt (The Merck Index 10th Ed., monograph no. 3434; PDR 38th Ed., pp. 1688–1689). Pirbuterol is a bronchodilator marketed or to be marketed around the world in the form of its dihydrochloride and monoacetate salts. See The Merck Index 10th Ed., monograph no. 7364. Its early synthesis and utility as a bronchodilator is disclosed in U.S. Pat. Nos. 3,700,681; 3,763,173; 3,772,314 and 3,786,160. Alternative and generally improved syntheses are found in U.S. Pat. Nos. 3,948,919; 4,011,231; and 4,031,108; Luxembourg Patent No. 79564; and European Patent Applications Nos. 58069, 58070, 58071 and 58072. More recently, pirbuterol has also found utility in the treatment of congestive heart failure (U.S. Pat. No. 4,175,128). Diazepam is a widely prescribed minor tranquilizer (The Merck Index 10th Ed., monograph no. 2967; PDR 38th Ed., pp. 1671–1674). Trimazosin (The Merck Index 10th Ed., monograph No. 9506) is an antihypertensive agent, marketed or to be marketed around the world as a hydrochloride salt, which is structurally related to prazosin.

The clinical value of the present improved formulation in inhibiting piroxicam-induced gastric irritation and ulcers is reflected by appropriate animal studies. Typical experimental protocols, in which the ability of the test compound to prevent or reduce piroxicam-induced gastric lesioning was determined, are found in the specific Examples below.

The present invention is readily carried out. The piroxicam or its salt is dosed in a mammal, particularly man, in the range of 0.1 to 1 mg/kg/day. The second medicinal agent can be dosed separately, in which case the latter will be employed in an amount within (but generally lower in) the dosage range and according to dosage regimens (frequency, routes and compositions) as specified for their alternative utility in the prior art, for example, in references cited above or further cited in said references.

Preferably and conveniently, the piroxicam and a gastric irritation and ulcer inhibiting agent of the present invention are co-administered in a single, combined formulation. This can be in a form suitable for parenteral administration, but is preferably in a form suitable for oral administration. The proportion of each drug in the combined dosage form will be in the ratio of the total daily dosage of each drug when dosed alone. The combined drugs will be dosed in single or divided doses. Single daily dosage will be most preferred in those cases where the in vivo half-life of the second medicinal agent is (like that of piroxicam) relatively long, and where the daily dosage of the second agent for a typical adult patient is relatively small, e.g., less than 1-2 grams.

In the preferred oral route of dosage, the amount of piroxicam (or salt equivalent) for an average adult patient will generally be in the range of 5–50 mg/day in combination with:
  200 to 4000 mg/day of acetaminophen;
  4 to 200 mg/day of doxepin;
  3 to 100 mg/day of pirbuterol;
  2 to 40 mg/day of diazepam; or
  4 to 500 mg/day of trimazosin;
an amount of the second medicinal agent generally sufficient to inhibit gastrointestinal irritation or ulcers which could otherwise be induced by the piroxicam in patients susceptible to this side effect.

The combined compounds are administered alone or in further combination with pharmaceutically-acceptable carriers or diluents. For oral use, suitable pharmaceutical carriers include inert diluents or fillers, thereby forming dosage forms such as tablets, powders, capsules, and the like. These pharmaceutical compositions can, if desired, contain additional ingredients such as flavorings, binders, excipients and the like. For example, tablets containing various excipients, such as sodium citrate, are employed, together with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials therefor include lactose or milk sugar and high molecular weight polyethylene glycols.

The present invention is illustrated by the following examples. However, it should be understood that the invention is not limited to the specific details of these examples.

EXAMPLE 1

Protective Effect of Various Medicinal Agents on Piroxicam-Induced Gastric Lesions in Rats Adult male "specific pathogen free" rats weighing 140–160 grams of the CD strain (Sprague-Dawley) were obtained from Charles River Breeding Laboratories (Kingston, N.Y.). The animals were acclimated for approximately one week and tested when they reached a body weight of 200–225 grams. The rats were fasted for 16 hours and randomized into groups consisting of 8 to 20 animals which were normalized with regard to their average body weight.

Gastric ulcers were induced in the animals by orally dosing them with a single 100 mg/kg dose of piroxicam in 2 ml. of aqueous 0.1% methylcellulose (pH=6.8). Those animals receiving a second medicinal agent separately received the second drug in an additional 2 ml. of the same medium at about the same time. Six and one-half hours later, the animals were sacrificed by cervical dislocation and autopsied. The stomachs were surgically removed, dissected along the greater curvature and rinsed with cold water. The stomachs were individually scored for both linear and punctate lesions. The total number of lesions was used for scoring purposes. The data obtained from each group of rats was analyzed after calculation of the mean number +/− the standard error of total gastric lesions. The values obtained were also compared to the controls which received only piroxicam by the two-tailed Student's T-Test for non-paired data. The protective effect of the second medicinal agent against piroxicam-induced ulcers is shown in Table I. These data show that pirbuterol, acetaminophen, doxepin and diazepam each significantly reduce piroxicam-induced gastric lesions in the healthy fasted rat.

TABLE I

Protective Effect of Various Medicinal Agents on Piroxicam-Induced Gastric Lesions in Rats[a]

| Medicinal Agent[a] | Oral Dose (mg/kg) | No. of Rats in Group | Lesions/Rat ($\bar{X}$ +/− SE)[b] | Significance p 0.05[c] |
|---|---|---|---|---|
| (Control) | — | 20 | 10.1 (1.5) | |
| Pirbuterol | 3.3 | 10 | 2.8 (0.9) | + |
| | 10 | 20 | 4.5 (1.1) | + |
| | 33 | 20 | 2.6 (0.7) | + |
| (Control) | — | 10 | 4.1 (1.0) | |
| Acetaminophen | 100 | 10 | 4.6 (1.9) | − |
| | 333 | 10 | 1.4 (0.7) | + |
| | 1000 | 10 | 0.7 (0.5) | + |
| (Control) | — | 20 | 9.5 (1.1) | |
| Doxepin | 3.3 | 10 | 4.4 (1.0) | + |
| | 10 | 10 | 3.6 (1.0) | + |
| | 33 | 20 | 4.2 (1.0) | + |
| (Control) | — | 20 | 9.3 (1.3) | |
| Diazepam | 10 | 20 | 5.6 (1.1) | + |
| | 33 | 20 | 4.2 (1.1) | + |

[a] All animals, including controls, received 100 mg/kg of piroxicam.
[b] Represents the mean value $\bar{X}$ +/− the standard error (SE).
[c] As determined by the Student's two tailed T-test for nonpaired data.

EXAMPLE 2

Protective Effect of Various Medicinal Agents on Gastric Lesions in Rats Induced by the Ethanolamine Salt of Piroxicam According to the preceeding Example, gastric ulcers were induced by a single dose of 100 or 120 mg./kg. of the ethanolamine salt of piroxicam. Test groups received various doses of various medicinal agents as shown in Table II. These data show that the test compounds showed a significant reduction in gastric lesions induced by the ethanolamine salt of piroxicam in healthy, fasted rats.

TABLE II

Protective Effect of Various Medicinal Agents on Gastric Lesions Induced by the Ethanolamine Salt of Piroxicam

| Medicinal Agent | Oral Dose (mg/kg) | No. of Rats in Group | Lesions/Rat ($\bar{X}$ +/− SE)[b] | Significance p<0.05[c] |
|---|---|---|---|---|
| (Control)[a] | — | 20 | 6.5 (0.9) | |
| Acetaminophen[a] | 100 | 20 | 4.8 (1.0) | − |
| | 333 | 20 | 0.9 (0.4) | + |
| | 1000 | 20 | 2.0 (2.3) | + |
| (Control)[a] | — | 30 | 7.7 (1.0) | |
| Doxepin[a] | 1.0 | 30 | 4.3 (0.7) | + |
| | 3.3 | 30 | 3.4 (0.6) | + |
| | 10 | 30 | 5.1 (0.8) | − |
| (Control)[a] | — | 10 | 6.4 (1.1) | |
| Diazepam[a] | 10 | 10 | 5.1 (0.9) | − |
| | 33 | 10 | 1.5 (0.7) | + |
| (Control)[d] | — | 10 | 7.6 (0.7) | |
| Trimazosin[d] | 3.3 | 10 | 5.0 (1.6) | − |
| | 10 | 10 | 3.9 (1.0) | + |

TABLE II-continued

Protective Effect of Various Medicinal Agents on Gastric Lesions Induced by the Ethanolamine Salt of Piroxicam

| Medicinal Agent | Oral Dose (mg/kg) | No. of Rats in Group | Lesions/Rat ($\bar{X}$ +/− SE)[b] | Significance p<0.05[c] |
|---|---|---|---|---|
| | 33 | 10 | 5.2 (1.3) | − |

[a] All animals, including controls, received 100 mg/kg of the ethanolamine salt of piroxicam.
[b] Represents the mean value $\bar{X}$ +/− the standard error (SE).
[c] As determined by the Student's two tailed T-test for non-paired data.
[d] All animals, including controls, received 120 mg/kg of the ethanolamine salt of piroxicam.

EXAMPLE 3

Protective Effect of Acetaminophen on Piroxicam-Induced Gastric Lesions in Rats

Male rats (Sprague-Dawley) having an average weight of 190 gms. were used in these studies. Animals were fasted overnight and then dosed with test compound suspended in 0.1% methylcellulose. Six and one-half hours after the administration of piroxicam or the combination, the rats were sacrificed in the same order as they were dosed. Their stomachs were excised, rinsed under running water and stored overnight between two saline soaked towels. The next morning the stomachs were evaluated and given an ulcer score. For each lesion a number was assigned according to size and another for intensity. The product of the two numbers is called the intensity factor, and the summation of the intensity factors represented the ulcer score for that stomach. Two separate (one was blind) runs were performed to obtain the data contained in Table III. The data show that acetaminophen attenuated the lesioning effect of 32 mg./kg. of piroxicam in healthy rats and that the protection is dose dependent.

Separate studies, in which piroxicam was dosed at 32 mg./kg., p.o. and acetaminophen at 250 mg./kg., p.o. or s.c., demonstrate that acetaminophen had no effect on the plasma levels of piroxicam.

Rats pre-dosed with acetaminophen (250 mg./kg., p.o.) at 16 and 3 hours before receiving piroxicam (32 ng./kg., p.o.), were not significantly protected from G.I. lesioning induced by the piroxicam under this protocol.

TABLE III

Dose Response of Acetaminophen With Piroxicam[a]

| Dose of Drug (mg/kg, p.o.) | | Number of Rats | Mean Ulcer Score + S.E.M. |
|---|---|---|---|
| piroxicam | acetaminophen | | |
| 0 | 0 | 4 | 0.0 ± 0.0 |
| 32 | 0 | 16 | 8.1 ± 0.8 |
| | | 10 | (14.0 ± 1.7) |
| 32 | 50 | 16 | 11.1 ± 1.6 |
| 32 | 100 | 16 | 10.2 ± 1.4 |
| | | 10 | (10.8 ± 0.8) |
| 32 | 200 | 16 | 2.7 ± 0.7 |
| 32 | 400 | 16 | 1.0 ± 0.4 |
| 32[b] | 800[b] | 16 | 1.2 ± 0.8 |
| 0 | 100 | 8 | 0.3 ± 0.2 |
| 0 | 320 | 16 | 0.7 ± 0.2 |

[a] This study was run blindly, except bracketed data, which was from a preliminary, unblinded study.
[b] Several of the rats dosed with 32 mg/kg of piroxicam and 800 mg/kg of acetaminophen had stomachs that were slightly distended with gas.

EXAMPLE 4

Prophylactic and Therapeutic Effect of Doxepin and Acetaminophen on Gastric Lesions in Rats Induced by the Ethanolamine Salt of Piroxicam Following the method of Examples 1 and 2, with sacrifice 6.5 hours post-dose of 100 mg/kg of the ethanolamine salt of piroxicam, the doxepin or acetaminophen were dosed prophylactically (8–24 hours prior to sacrifice) or therapeutically (1 to 4 hours prior to sacrifice). Results are shown in Table IV. Under this protocol, acetaminophen showed consistent protective activity when dosed 1.5 hours prior to piroxicam administration.

TABLE IV

Prophylactic and Therapeutic Properties of Doxepin and Acetaminophen on Gastric Lesions Induced by the Ethanolamine Salt of Piroxicam[a]

| Compound Tested[a] | Time(hours) Prior to Sacrifice | Oral Dose mg/kg | Lesions/Rat X ± (SE) | Significance p <0.05 |
|---|---|---|---|---|
| (Control) | — | — | 8.8 (2.2) | |
| Doxepin | 24 | 1.0 | 4.9 (1.5) | — |
| | | 3.3 | 8.8 (1.6) | — |
| (Prophylactic- | | 10.0 | 4.7 (2.2) | — |
| prior to | 20.5 | 1.0 | 7.0 (1.6) | — |
| piroxicam | | 3.3 | 10.5 (2.5) | — |
| administration) | | 10.0 | 7.3 (1.1) | — |
| | 8.0 | 1.0 | 4.6 (0.9) | — |
| | | 3.3 | 4.4 (1.6) | — |
| | | 10.0 | 5.2 (1.0) | — |
| (Control) | — | — | 7.3 (1.2) | |
| Doxepin | 4.0 | 1.0 | 3.0 (1.1) | + |
| | | 3.3 | 3.6 (1.1) | + |
| (Therapeutic- | | 10.0 | 3.2 (1.3) | + |
| after | 2.5 | 1.0 | 2.2 (0.8) | + |
| piroxicam | | 3.3 | 4.1 (1.3) | — |
| administration) | | 10.0 | 3.1 (0.9) | + |
| | 1.0 | 1.0 | 3.5 (1.2) | + |
| | | 3.3 | 6.6 (1.2) | — |
| | | 10.0 | 7.0 (1.1) | — |
| (Control) | — | — | 6.2 (0.9) | |
| Acetaminophen | 20.5 | 100 | 3.9 (1.1) | + |
| | | 333 | 9.8 (1.5) | — |
| (Prophylactic) | | 1000 | 12.4 (2.0) | — |
| | 8.0 | 100 | 2.7 (1.0) | + |
| | | 333 | 2.2 (0.8) | + |
| | | 1000 | 2.9 (1.0) | + |

[a] All animals, including controls, received 100 mg/kg of the ethanolamine salt of piroxicam 6.5 hours before sacrifice.

EXAMPLE 5

Capsules Piroxicam (20 mg) and Acetaminophen (1000 mg)

The following ingredients are combined in the following proportions by weight:

| | |
|---|---|
| piroxicam (milled) | 20 |
| acetaminophen (milled) | 1000 |
| calcium carbonate | 250 |
| polyethylene glycol, average molecular weight, 4000 | 430 |

The mixture is thoroughly blended so as to obtain a uniform powder. Soft gelatin capsules containing 20 mg. of piroxicam and 1000 mg. of acetaminophen are prepared by filling suitably sized capsules with 1700 mg of the blend.

To make hard gelatin filled capsules, the amount of inert ingredients is adjusted so as to conveniently fill standard sized gelatin capsules containing the desired amount of each active component.

EXAMPLE 6

Capsules—Piroxicam (10 mg) and Acetaminophen (500 mg)

The following ingredients are combined in the following proportions by weight:

| | | |
|---|---|---|
| piroxicam ethanolamine salt (milled) | 11.84 | (equivalent to 10 as free acid) |
| acetaminophen (milled) | 500 | |
| corn starch | 485.16 | |
| magnesium stearate | 3 | |

The mixture is thoroughly blended so as to form a uniform powder. The resultant mix is filled into appropriately sized hard gelatin capsules (fill weight 1000 mg) so as to obtain capsules containing the desired potency of each active ingredient.

EXAMPLE 7

Capsules—Piroxicam (20 mg) and Doxepin (15 mg)

The following ingredients are combined in the following proportions by weight:

| | | |
|---|---|---|
| piroxicam (milled) | 20 | |
| doxepin hydrochloride | 16 | (equivalent to 15 of free base) |
| polyethylene glycol, average molecular weight, 4000 | 664 | |

The mixture is thoroughly blended so as to obtain a uniform powder. The resultant mix (700 mg fill weight) is filled into hard gelatin capsules of a suitable size so as to obtain capsules of the desired potency.

EXAMPLE 8

Capsules—Piroxicam (20 mg) and Doxepin (50 mg)

The following ingredient are combined in the following proportions by weight:

| | | |
|---|---|---|
| piroxicam (milled) | 20 | |
| doxepin hydrochloride (milled) | 53.3 | (equivalent to 50 of free base) |
| corn starch | 633.7 | |
| magnesium stearate | 3 | |

The mixture is thoroughly blended to form a uniform powder which is filled into size 0 hard gelatin capsules (fill weight 700 mg) to obtain capsules containing the desired potency of each ingredient.

EXAMPLE 9

Tablets—Piroxicam (20 mg) and Doxepin (20 mg)

The following ingredients are combined in the following proportions by weight:

| | | |
|---|---|---|
| piroxicam (milled) | 20 | |
| doxepin hydrochloride (milled) | 21.3 | (equivalent to 20 of free base) |
| lactose | 186.7 | |
| hydroxypropyl methylcellulose | 3 | |
| sodium starch glycollate | 15 | |
| magnesium stearate | 4 | |

The mixture is thoroughly blended to form a uniform powder. Measured volumes of the powder, corresponding to 250 mg by weight, are compressed into tablets containing the desired potency of each active ingredient.

EXAMPLE 10

Tablets—Piroxicam (10 mg) and Pirbuterol (25 mg)

The following ingredients are combined in the following proportions by weight:

| | |
|---|---|
| piroxicam ethanolamine salt (milled) | 23.68 (equivalent to 20 of free base) |
| pirbuterol acetate | 31.28 (equivalent to 25 of free base) |
| lactose | 220.04 |
| hydroxypropyl methylcellulose | 4 |
| sodium starch glycollate | 16 |
| magnesium stearate | 5 |

The mixture is thoroughly blended to form a uniform powder. The powder, in measured volumes corresponding to 300 mg. by weight, is compressed into tablets containing the desired potency of each active ingredient.

EXAMPLE 11

Capsules—Piroxicam (20 mg) and Pirbuterol (20 mg)

The following ingredients are combined in the following proportions by weight:

| | | |
|---|---|---|
| piroxicam (milled) | 20 | |
| pirbuterol dihydrochloride (milled) | 26.1 | (equivalent to 20 of free base) |
| cornstarch | 652.9 | |
| magnesium stearate | 3 | |

The mixture is thoroughly blended so as to obtain a uniform powder. The resultant mix (700 mg fill weight) is filled into hard gelatin capsules of a suitable size so as to obtain capsules of the desired potency.

Equivalent proportions of piroxicam ethanolamine salt (23.7) and pirbuterol monoacetate (23.4) are combined with cornstarch and magnesium stearate and filled into hard gelatin capsules in like manner to obtain capsules containing the same potency of each active ingredient.

EXAMPLE 12

Capsules—Piroxicam (20 mg) and Diazepam (10 mg)

The following ingredients are combined in the following proportion by weight:

| | | |
|---|---|---|
| piroxicam ethanolamine salt | 23.68 | (equivalent to 20 of free acid) |
| diazepam | 10 | |
| calcium carbonate | 50 | |
| polyethylene glycol, average molecular weight, 4000 | 166.32 | |

The mixture is blended to a uniform power and filled (250 mg fill weight) into hard gelatin capsules of a suitable size to obtain capsules of the desired potencies.

EXAMPLE 13

Tablets—Piroxicam (10 mg) and Diazepam (5 mg)

The following ingredients are combined in the following proportions by weight:

| | |
|---|---|
| piroxicam | 10 |
| diazepam | 5 |
| lactose | 123 |
| hydroxypropyl methylcellulose | 2 |
| sodium starch glycollate | 8 |
| magnesium stearate | 2 |

The mixture is thoroughly blended to form a uniform powder. Measure volumes of the powder, corresponding to 150 mg by weight, are compressed into tablets containing the desired potency of each active ingredient.

EXAMPLE 14

Tablets—Piroxicam (20 mg) and Acetaminophen (500 mg)

The following ingredients are combined in the following proportions by weight:

| | |
|---|---|
| piroxicam | 20 |
| acetaminophen | 500 |
| lactose | 1035 |
| hydroxypropyl methylcellulose | 10 |
| sodium starch glycollate | 25 |
| magnesium stearate | 10 |

The mixture is blended to a uniform powder and compressed into tablets in measured volumes corresponding to 1600 mg by weight to yield tablets of the desired potency in each drug.

EXAMPLE 15

Capsules—Piroxicam (20 mg) and Trimázosin (40 mg)

The following ingredients are combined in the following proportions by weight:

| | | |
|---|---|---|
| piroxicam | 20 | |
| trimazosin hydrochloride monohydrate | 45 | (equivalent to 40 of free base) |
| cornstarch | 632 | |
| magnesium stearate | 3 | |

The mixture is thoroughly blended so as to obtain a uniform powder. The resultant mix (700 mg fill weight) is filled into hard gelatin capsules of a suitable size so as to obtain capsules of the desired potency in each drug.

We claim:

1. An improved method for the treatment of inflammation in a mammal which comprises, in addition to treatment with an antiinflammatory amount of piroxicam, or a pharmaceutically acceptable salt thereof, treatment with a gastric antiirritation and ulcer-inhibiting amount of pirbuterol, or a pharmaceutically acceptable salt thereof.

2. A method of claim 1 wherein the pirbuterol is in the form of its dihydrochloride salt and the piroxicam is in its free enolic form.

3. A method of claim 1 wherein the pirbuterol is in the form of its monoacetate salt and the piroxicam is in the form of its ethanolamine salt.

4. An improved antiinflammatory composition which comprises:
   (a) an antiinflammatory amount of piroxicam, or a pharmaceutically acceptable salt thereof; and
   (b) a gastric antiirritation and ulcer-inhibiting amount of pirbuterol, or a pharmaceutically acceptable salt thereof.

5. A composition of claim 4 wherein the pirbuterol is in the form of its dihydrochloride salt and the piroxicam is in its free enolic form.

6. A composition of claim 4 wherein the pirbuterol is in the form is its monoacetate salt and the piroxicam is in the form of its ethanolamine salt.

* * * * *